United States Patent
Treacy et al.

(10) Patent No.: US 10,004,620 B2
(45) Date of Patent: Jun. 26, 2018

(54) SUTURE AND WIRE STENT DEPLOYMENT SYSTEM

(71) Applicant: Cook Medical Technologies LLC, Bloomington, IN (US)

(72) Inventors: Gerard Treacy, Limerick (IE); Vincent McHugo, Birdhill (IE); Triona Campbell, Shannonview (IE)

(73) Assignee: Cook Medical Technologies LLC, Bloomington, IN (US)

( * ) Notice: Subject to any disclaimer, the term of this patent is extended or adjusted under 35 U.S.C. 154(b) by 254 days.

(21) Appl. No.: 14/992,449

(22) Filed: Jan. 11, 2016

(65) Prior Publication Data
US 2016/0199207 A1 Jul. 14, 2016

Related U.S. Application Data

(60) Provisional application No. 62/103,156, filed on Jan. 14, 2015.

(51) Int. Cl.
*A61F 2/06* (2013.01)
*A61F 2/95* (2013.01)
*A61F 2/82* (2013.01)
*A61F 2/97* (2013.01)

(52) U.S. Cl.
CPC .................. *A61F 2/95* (2013.01); *A61F 2/82* (2013.01); *A61F 2/97* (2013.01); *A61F 2002/9505* (2013.01); *A61F 2002/9511* (2013.01); *A61F 2002/9528* (2013.01); *A61F 2210/0004* (2013.01)

(58) Field of Classification Search
CPC ...... A61F 2/82; A61F 2/95; A61F 2/97; A61F 2002/9505; A61F 2002/9511; A61F 2002/9528
See application file for complete search history.

(56) References Cited

U.S. PATENT DOCUMENTS

| | | |
|---|---|---|
| 5,405,378 A | 5/1995 | Strecker |
| 6,302,891 B1 | 10/2001 | Nadal |
| 6,471,722 B1 * | 10/2002 | Inoue ................ A61F 2/07 623/1.16 |
| 6,514,285 B1 | 2/2003 | Pinchasik |
| 6,733,521 B2 | 5/2004 | Chobotov et al. |

(Continued)

FOREIGN PATENT DOCUMENTS

| | | | |
|---|---|---|---|
| AU | 2012258395 B1 * | 3/2013 | ............ A61F 2/07 |
| EP | 2 735 283 A1 | 5/2014 | |
| WO | WO 2009/126227 A2 | 10/2009 | |

OTHER PUBLICATIONS

International Search Report and Written Opinion for related application No. PCT/US2016/012795 (11 pgs).

*Primary Examiner* — Robert Lynch
(74) *Attorney, Agent, or Firm* — Brinks Gilson & Lione

(57) ABSTRACT

A stent delivery system is provided that includes a self-expanding stent with a longitudinal length and a plurality of individual suture loops spaced along the longitudinal length of the stent, wherein the stent is compressed by the plurality of individual suture loops. The stent delivery system also includes a longitudinal pull member that secures the plurality of individual suture loops about the stent, wherein the plurality of individual suture loops are configured to separate from about the stent when the longitudinal pull wire is removed.

16 Claims, 4 Drawing Sheets

(56) References Cited

U.S. PATENT DOCUMENTS

| | | |
|---|---|---|
| 7,320,703 B2 | 1/2008 | DiMatteo et al. |
| 8,057,533 B2 | 11/2011 | Mangin et al. |
| 8,784,474 B2 | 7/2014 | Sargent, Jr. |
| 2007/0043425 A1* | 2/2007 | Hartley .................... A61F 2/07 623/1.12 |
| 2008/0039924 A1 | 2/2008 | Peacock |
| 2008/0177368 A1 | 7/2008 | Goto |
| 2012/0022630 A1 | 1/2012 | Wubbeling |
| 2013/0006347 A1* | 1/2013 | McHugo .................... A61F 2/95 623/1.12 |
| 2013/0090714 A1 | 4/2013 | McHugo |

* cited by examiner

SUTURE AND WIRE STENT DEPLOYMENT SYSTEM

CROSS-REFERENCE TO RELATED APPLICATIONS

The present patent document claims the benefit of the filing date under 35 U.S.C. § 119(e) of Provisional U.S. Patent Application Ser. No. 62/103,156 filed Jan. 14, 2015, which is hereby incorporated by reference.

FIELD

The present disclosure relates to medical devices and more specifically to delivery systems for self-expanding stents.

BACKGROUND

The statements in this section merely provide background information related to the present disclosure and may not constitute prior art.

Self-expanding stents are medical devices used to treat diseased areas of a variety of body lumens, including, but not limited to: veins, esophagi, bile ducts, colons, and ureters. Generally, self-expanding stents are inserted into a body lumen with a delivery system to help support a weak point in the body lumen or to bypass it completely. A self-expanding stent is a tubular structure with at least one lumen that runs through it. Self-expanding stents are often made of a wire or mesh material that can elastically contract and expand.

A self-expanding stent usually has two states: a delivery state and a deployed state. In the delivery state, the self-expanding stent is radially compressed to a smaller diameter to allow the self-expanding stent to be delivered through a body lumen to the diseased area. Once the self-expanding stent is positioned at the diseased area, the self-expanding stent is then radially expanded to a larger diameter into a deployed state. Once in the deployed state, the self-expanding stent is secured to the walls of the body lumen through friction or is attached to the wall of the body lumen using various methods. Depending on the application, the deployed self-expanding stent then maintains the structure of a weakened body lumen wall or creates a new fluid channel to bypass the diseased area.

Self-expanding stents are manufactured to naturally tend towards an expanded, deployed state. Prior to insertion into the body lumen, self-expanding stents are generally radially compressed to a delivery state, and will naturally expand back to a deployed state once the means used to compress the stent is removed. Often, the self-expanding stent is compressed using an outer sheath: a simple tubular structure with a lumen running through it. The self-expanding stent is placed within the lumen of the outer sheath, which radially compresses it into the delivery state. Once the self-expanding stent is in position within the body lumen, the outer sheath is removed from the stent and the stent expands into its deployed state.

While using an outer sheath to deliver a self-expanding stent is common, it has several disadvantages. For example, as the stent is compressed to a smaller diameter, a greater deployment force is required to remove the outer sheath from the stent and thus deploy the stent. If the force required to remove the outer sheath from the stent is too high, positioning difficulties as well as potential damage to the body lumen could occur. Therefore, the stent can only be compressed to a certain diameter when using an outer sheath. Additionally, self-expanding stents are typically expanded by pulling the outer sheath from the distal end of the stent to the proximal end, meaning the distal end of the stent expands first and the proximal end last. This limitation can lead to inaccurate placement of the stent. In addition, high frictional forces during withdrawal of the outer sheath may damage the stent. Therefore, it is desirable to provide a device that improves on these disadvantages.

SUMMARY

In one form of the present disclosure, a stent delivery system is provided comprising a self-expanding stent and a plurality of individual suture loops spaced along a longitudinal length of the stent. The stent is compressed by the plurality of individual suture loops. The stent delivery system further comprises a longitudinal pull member securing the plurality of individual suture loops about the stent. The plurality of individual suture loops are configured to separate from about the stent when the longitudinal pull member is removed. This embodiment may also include an elongate delivery catheter, wherein the self-expanding stent is removably disposed about the delivery catheter. The stent delivery system may also include a longitudinal retrieval member connected to the plurality of individual suture loops.

In another form of the present disclosure, the stent delivery system further includes the plurality of individual suture loops comprising a first set of suture loops and a second set of suture loops. The longitudinal pull member further comprises a first individually movable pull member and a second individually movable pull member. The first individually movable pull member secures the first set of suture loops about the self-expandable stent and the second individually movable pull member secures the second set of suture loops about the self-expandable stent. Additionally, the first set of suture loops is configured to separate from about the self-expanding stent when the first individually movable pull member is removed, and the second set of suture loops is configured to separate from about the self-expanding stent when the second individually movable pull member is removed In still another form of the present disclosure, a method of delivering a stent is provided comprising providing a stent delivery system comprising a self-expanding stent comprising a longitudinal length, and a plurality of individual suture loops spaced along the longitudinal length of the self-expanding stent. The self-expanding stent is compressed by the plurality of individual suture loops, and a longitudinal pull member secures the plurality of individual suture loops about the self-expanding stent. The plurality of individual suture loops are configured to separate from about the self-expanding stent when the longitudinal pull member is removed. The method further comprises inserting the stent delivery system in a compressed state into a body lumen. The method also comprises expanding the self-expanding stent to an expanded state by removing the longitudinal pull member to separate the plurality of individual suture loops from about the self-expanding stent. This method can also include providing a longitudinal retrieval member connected to the plurality of individual suture loops and removing the plurality of individual suture loops from the body lumen by extracting the longitudinal retrieval member.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
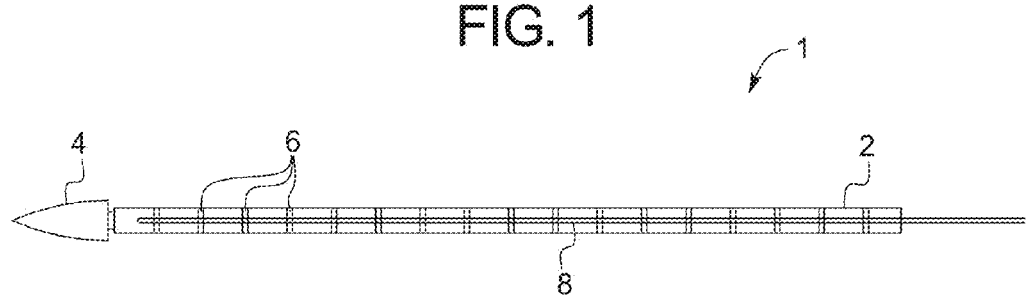
FIG. 1 is an illustration of the stent deployment system constructed in accordance with the teachings of the present disclosure.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

Figure 2:
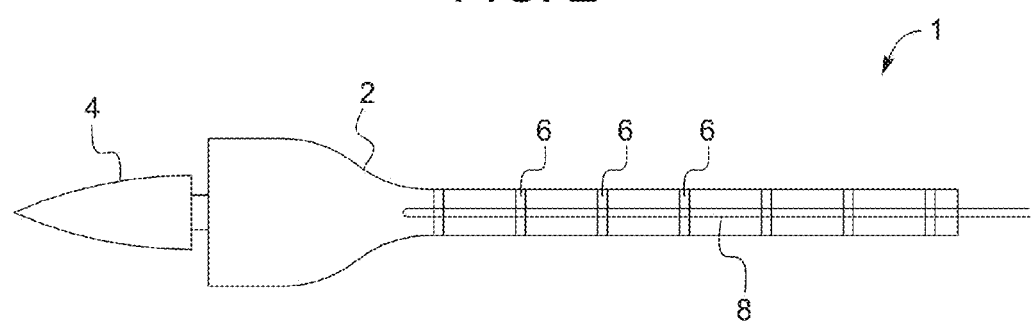
FIG. 2 is another illustration of the stent deployment system.

Referring to FIGS. 1 and 2, a stent introducer system 1 is provided. FIG. 1 shows a self-expandable stent 2 in a compressed, or delivery, state; while FIG. 2 shows the self-expandable stent 2 partially expanded into a deployed state. A carrier tube 4 may be placed within a lumen of the self-expandable stent 2. The self-expandable stent 2 is compressed by multiple suture loops 6 spaced along the length of the self-expandable stent 2. The suture loops 6 are secured about the self-expandable stent 2 with the help of a longitudinal pull member 8. The longitudinal pull member is ideally flexible and made from a biocompatible material such as, but not limited to, stainless steel, nitinol, cobalt alloys, titanium alloys, polytetrafluoroethylene, nylon, and high-density polyethylene.

Figure 3A:
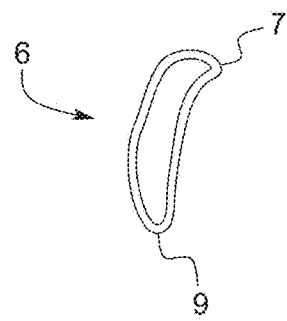
FIG. 3A is a detailed view of one embodiment of the suture loops.
Figure 3B:
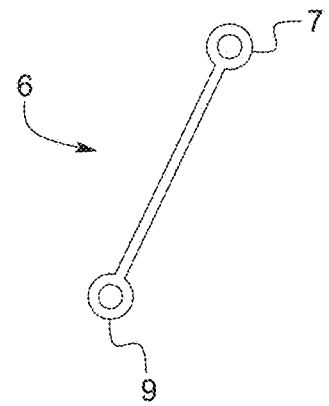
FIG. 3B is a detailed view of another embodiment of the suture loops.

Referring to FIGS. 3A and 3B, two embodiments of the suture loop 6 are provided. In FIG. 3A, the suture loop 6 is a flexible loop that can be made from numerous materials including, but not limited to, any combination of biocompatible materials such as suture thread, wire, stainless steel, nitinol, cobalt alloys, titanium alloys, polytetrafluoroethylene, nylon, and high-density polyethylene. In FIG. 3B, the suture loop 6 is a flexible member with closed loops on each end that can be made from numerous materials including, but not limited to, any combination of biocompatible materials such as suture thread, wire, stainless steel, nitinol, cobalt alloys, titanium alloys, polytetrafluoroethylene, nylon, and high-density polyethylene. In both embodiments, the suture loop 6 can also be made of a biodegradable material that can be safely released into the body after the self-expandable stent 2 is deployed. In each embodiment, the suture loop 6 has a first end 7 and a second end 9.

Figure 4:
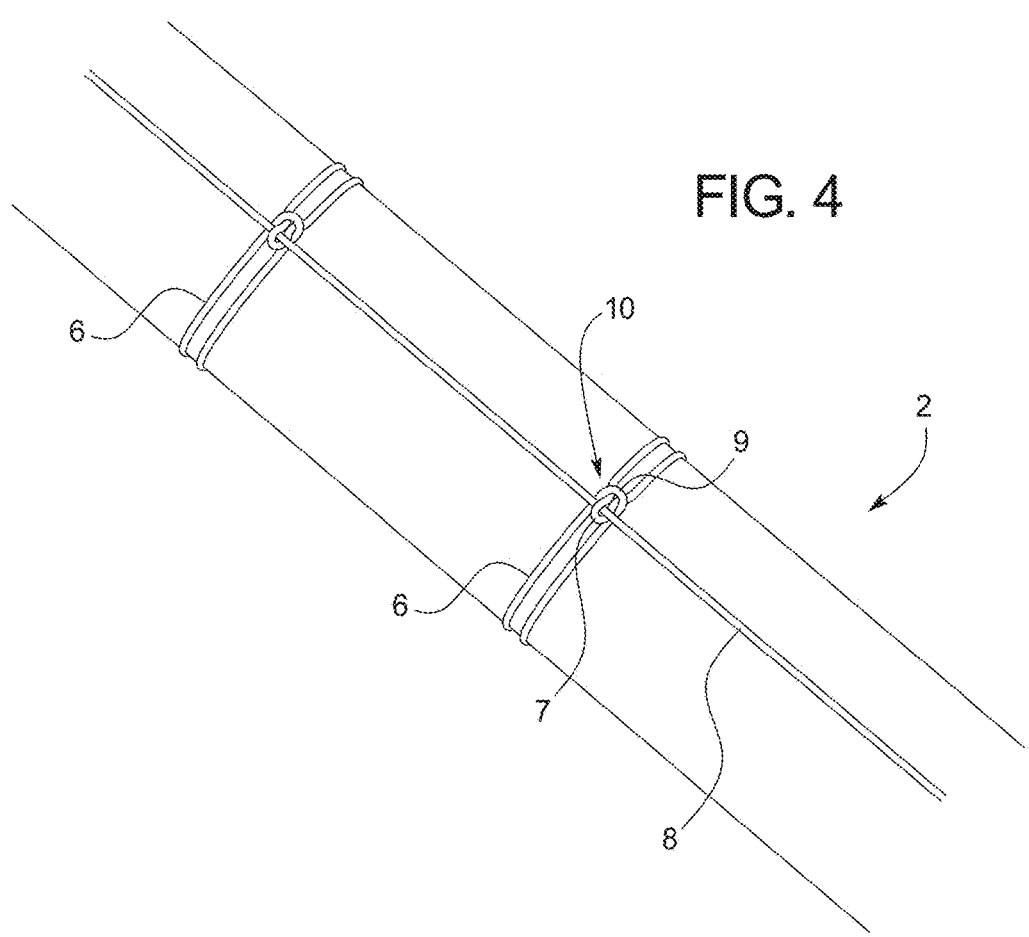
FIG. 4 is a detailed view of the suture loops and longitudinal pull member on the self-expandable stent.

FIG. 4 shows a detailed view of the self-expandable stent 2. Each suture loop 6 is folded in half and then wrapped around the self-expandable stent 2 to create a connection point 10 where the first end 7 and the second end 9 meet. The first end 7 of the suture loop 6 may then be pulled through the second end 9 of the suture loop at the connection point 10. The longitudinal pull member 8 is then fed through the first end 7 of the suture loop 6 to secure the suture loop 6 to the self-expandable stent 2 and maintain the self-expandable stent 2 in a compressed state. Alternatively, the longitudinal pull member 8 may be fed through the first end 7 and the second end 9 of the suture loop 6 separately, thereby securing the suture loop 6 to the self-expandable stent 2 and maintaining the self-expandable stent 2 in a compressed state. This process may be repeated until all of the suture loops 6 are secured to the self-expandable stent 2 and the self-expandable stent 2 is fully compressed. The longitudinal pull member 8 preferably extends from at least the most distal suture loop 6 to a point external from the patient when the self-expandable stent 2 is at the diseased area. To ensure that the longitudinal pull member 8 secures the suture loops 6 about the self-expandable stent 2, a stiffer material, such as a biocompatible metal, may be used for the longitudinal pull member 8 at the connection points 10. Then, a more flexible material may be used for the rest of the longitudinal pull member 8 to ensure easy withdrawal of the longitudinal pull member 8 from the patient.

Figure 5:
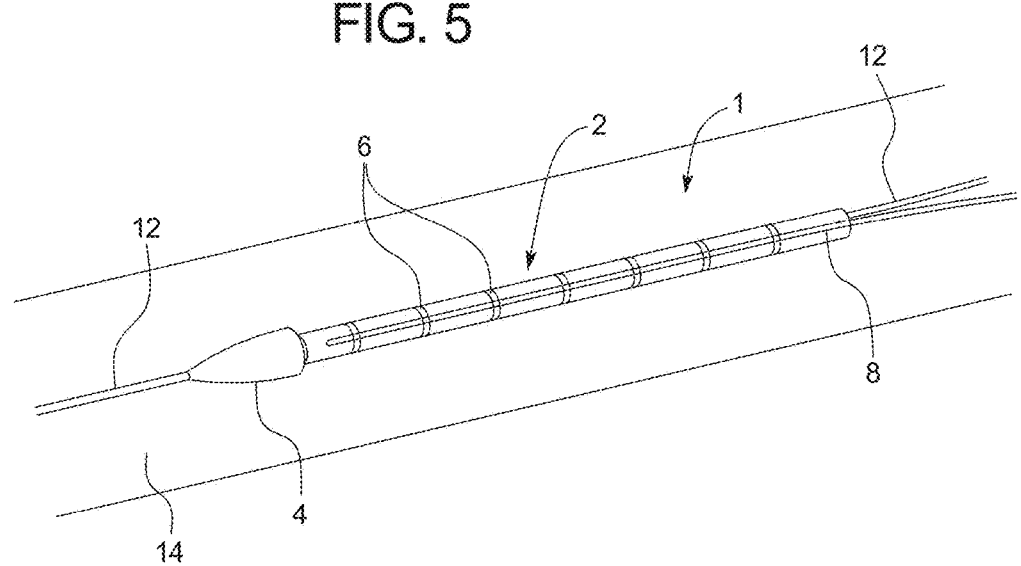
FIG. 5 is an illustration of the method of deploying the self-expanding stent in a body lumen.

Now referring to FIG. 5, once the self-expandable stent 2 is compressed into the delivery state, the stent introducer system 1 may be fed as a single unit over a guide wire 12 into a body lumen 14. The self-expandable stent 2 is advanced along the guide wire 12 until it reaches the diseased area. Once at the diseased area, the longitudinal pull member 8 may be retracted from the self-expandable stent 2. As shown in FIG. 2, as the distal end of the longitudinal pull member 8 is retracted past the connection point 10 of each suture loop 6, the suture loops 6 will separate from about the self-expandable stent 2, allowing the self-expandable stent 2 to expand into its deployed position. Once all of the suture loops 6 have separated from about the self-expandable stent 2, the self-expandable stent will be fully deployed. The carrier tube 4, guide wire 12, and longitudinal pull member 8 may then be removed from the body.

With this design, the stent introducer system 1 may have a lower profile in the delivery state while maintaining a low and manageable deployment force. Particularly, the self-expandable stent 2 may be radially compressed to a diameter smaller than when using an outer sheath, thus making it easier for the clinician to feed the stent introducer system 1 through the body lumen 14. Additionally, the deployment force for this design may be lower than a comparable outer sheath deployment design, thus making it easier for the clinician to deploy the self-expandable stent 2 at the diseased area. The lower profile and deployment force may also make the entire procedure less traumatic for the patient.

Figure 6:
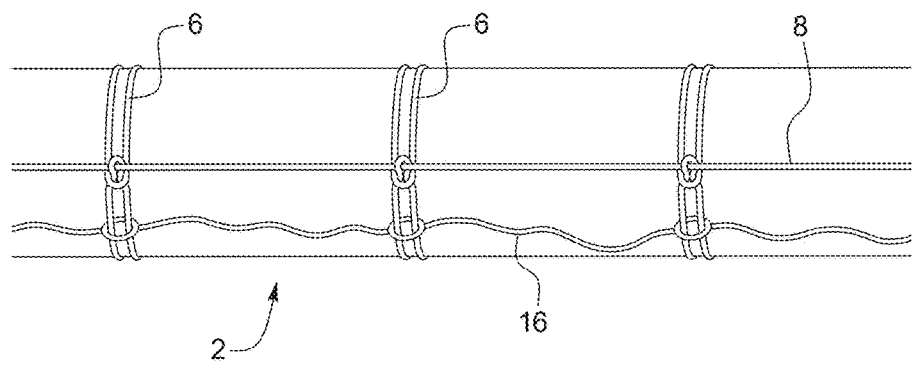
FIG. 6 is a detailed view of the retrieval member on the self-expanding stent.

The suture loops 6 may be designed to be biodegradable and, once separated from about the self-expandable stent 2, will dissolve or be absorbed safely into the body. The suture loops 6 may also remain attached to the self-expandable stent 2 after separation from about the self-expandable stent 2. Alternatively, as shown in FIG. 6, the suture loops 6 may be attached to a retrieval member 16. The suture loops 6 are preferably connected to the retrieval member 16 by simple knots, although other methods may be used. The retrieval member 16 is separate and distinct from the longitudinal pull member 8, and may be made of a flexible, biocompatible material including, but not limited to, any combination of biocompatible materials such as suture thread, wire, stainless steel, nitinol, cobalt alloys, titanium alloys, polytetrafluoroethylene, nylon, and high-density polyethylene. The retrieval member 16 preferably extends from at least the most distal suture loop 6 to a point external from the patient when the self-expanding stent 2 is at the diseased area. When the longitudinal pull member 8 is removed from the self-expandable stent 2, the suture loops 6 remain attached to the retrieval member 16 and can then be retrieved from the body lumen 14 by extracting the retrieval member 16 from the body. Alternatively, the retrieval member 16 may be tethered to the carrier tube 4, so that the retrieval member 16 along with the attached suture loops 6 may be removed from the body when the carrier tube 4 is removed.

Figure 7:
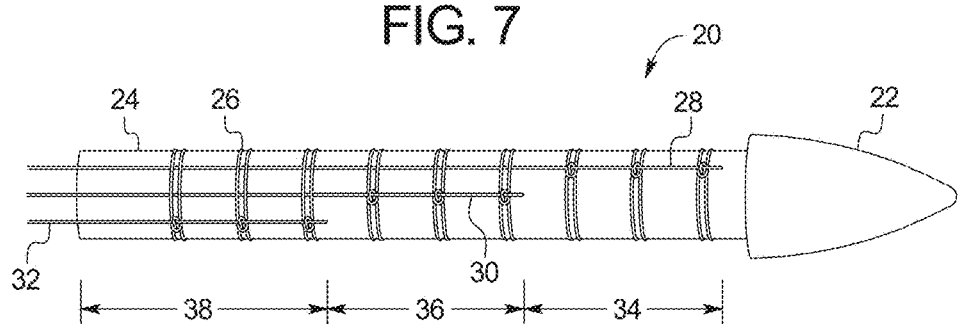
FIG. 7 is an illustration of the stent deployment system with multiple pull members.

FIG. 7 shows another embodiment of the invention. In this embodiment, a stent introducer system 20 is provided. The stent introducer system 20 includes a delivery catheter 22 oriented within a lumen of a self-expandable stent 24. The self-expandable stent 24 is compressed by multiple suture loops 26. However, in contrast to the single pull member in previous embodiments, multiple pull members are provided: a distal pull member 28, a central pull member 30, and a proximal pull member 32. The self-expandable stent 24 has three portions corresponding to each pull member: a distal portion 34, a central portion 36, and a proximal portion 38. Each pull member secures the suture loops 26 in each corresponding portion to the self-expandable stent 24: for example the distal pull member 28 secures the suture loops 26 on the distal portion 34 of the self-expanding stent 24. There may be multiple suture loops 26 in each stent portion, or only a single suture loop 26 corresponding to each stent portion. This arrangement allows a clinician to control in what order the portions of the self-expandable stent 24 are deployed.

Figure 8:
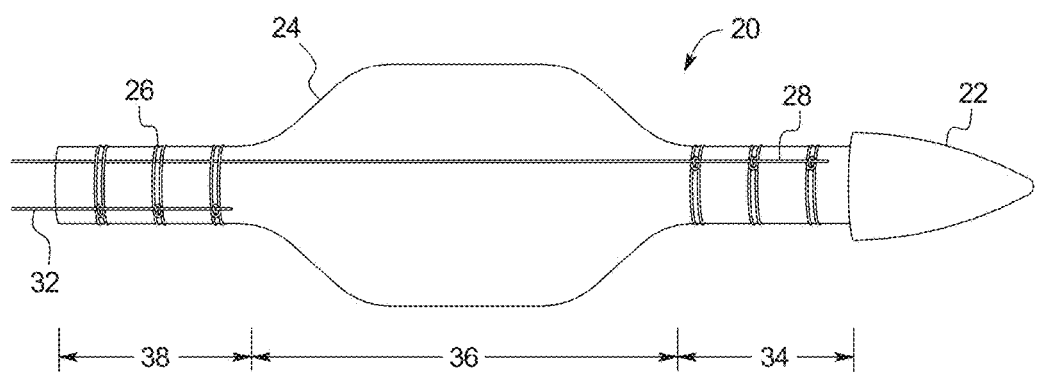
FIG. 8 is another illustration of the stent deployment system with multiple pull members.

For example, in FIG. 8, the central portion 36 of the self-expandable stent 24 is deployed first by retracting the central pull member 30 from the self-expanding stent 24, causing the suture loops 26 in the central portion 36 to separate from about the self-expandable stent 24. Since the distal pull member 28 and the proximal pull member 32 have not been retracted, the distal portion 34 and proximal portion 38 remain compressed. The distal portion 38 and proximal portion 34 of the self-expandable stent 24 may now be expanded in turn by retracting each portion's respective pull member. This flexibility allows the operator to maintain greater precision over the deployment of the self-expandable stent 24. While this embodiment describes three stent portions that can be expanded individually, any number of stent portions and corresponding pull members can be contemplated with the present invention.

Figure 9:
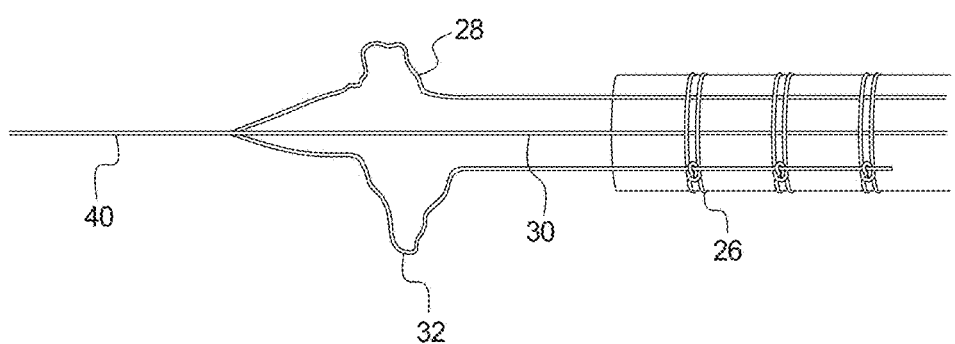
FIG. 9 is an illustration of the stent deployment system with a main pull member.

Referring to FIG. 9, a main pull member 40 may be used to connect the multiple pull members together. In this embodiment, the distal pull member 28, central pull member 30, and proximal pull member 32, all join into a single, main pull member 40 at a point proximal from the self-expandable stent 24. The main pull member 40 then extends to a point external of the patient. The main pull member 40 may then be withdrawn from the patient, thus deploying all three portions of the self-expandable stent 24 with a single motion. Additionally, one or more of the pull members may have a predetermined amount of slack built into the stent deployment system to further control in what order the portions of the self-expandable stent 24 are deployed. In FIG. 9, both the distal pull member 28 and proximal pull member 32 have built in slack, while the central pull member 30 does not. Thus, as the main pull member 40 begins to be withdrawn from the patient, the central pull member 30 will also be withdrawn and the suture loops 26 in the central portion 36 of the self-expandable stent 2 will begin to separate from about the self-expandable stent 24, thus causing the central portion 36 to deploy. However, because of the built in slack, the distal pull member 28 and proximal pull member 32 will not cause their respective portions to deploy until the main pull member 40 is retracted to a point where the built in slack is eliminated. In this embodiment, the point at which the slack is eliminated is after the central portion 36 is fully deployed. Thus, once this point is reached and the central portion 36 is fully deployed, the distal portion 34 and proximal portion 38 will then begin to deploy as the main pull member 40 continues to be withdrawn from the patient. With this embodiment, a controlled deployment can still be attained while eliminating the need to withdraw the multiple pull wires separately. While this embodiment contemplates a self-expandable stent 2 that deploys the central portion 36 first, any other order of deployment can be contemplated by adjusting which pull members have built in slack.

Additionally, the retrieval member 16 shown in FIG. 6 may be incorporated into the embodiment shown in FIGS. 7 and 8. A single retrieval member 16 may be attached to all of the suture loops 26, or multiple retrieval members 16 may be connected to the suture loops 26 in each corresponding portion of the self-expandable stent 24. Therefore, each section of suture loops 26 may be removed as the corresponding portion of the self-expandable stent 24 is expanded. Alternatively, the suture loops 26 may be biodegradable and release into the body upon separation from about the self-expandable stent 24, or the suture loops 26 may remain secured to the self-expandable stent 24 after the self-expandable stent 24 is expanded.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:
1. A stent delivery system, comprising:
a self-expanding stent comprising a longitudinal length;
an elongate delivery catheter, wherein the self-expanding stent is removably disposed about the delivery catheter,
a plurality of individual suture loops spaced along the longitudinal length of the self-expanding stent, wherein the self-expanding stent is compressed by the plurality of individual suture loops, the suture loops comprise a first set of suture loops and a second set of suture loops;
a first longitudinal pull member securing the plurality of individual first set of suture loops about the self-expanding stent, and a second longitudinal pull member securing the second set of suture loops about the self-expanding stent, wherein the first set of suture loops are configured to separate from about the self-expanding stent when the first longitudinal pull member is removed, and the second set of suture loops is configured to separate from about the self-expanding stent when the second individually movable pull member is removed; and a main pull member, the main pull member connected to the first individually movable pull member and the second individually movable pull member.

2. The stent delivery system of claim 1, wherein:
the plurality of individual suture loops comprise a biodegradable material.

3. The stent delivery system of claim 1, wherein:
the longitudinal pull member comprises a flexible, biocompatible material.

4. The stent delivery system of claim 1, wherein:
the self-expanding stent is an esophageal stent.

5. The stent delivery system of claim 1, further comprising:
a longitudinal retrieval member connected to the plurality of individual suture loops.

6. The stent delivery system of claim 1, wherein:
the self-expanding stent further comprises a delivery state wherein the self-expanding stent is compressed by the plurality of individual suture loops; and
the self-expanding stent further comprises a deployed state wherein the plurality of individual suture loops are separated from about the self-expanding stent allowing the self-expanding stent to revert to a non-compressed state.

7. The stent delivery system of claim 6, wherein:
the self-expanding stent further comprises an outer diameter, wherein the outer diameter of the self-expanding stent during the delivery state is smaller than the outer diameter of the self-expanding stent during the deployed state.

8. The stent delivery system of claim 1, further comprising:
a longitudinal retrieval member connected to the first and second sets of suture loops.

9. The stent delivery system of claim 1, wherein:
the self-expanding stent further comprises a delivery state wherein the self-expanding stent is compressed by the first and second sets of suture loops; and
the self-expanding stent further comprises a deployed state wherein the first and second sets of suture loops are separated from about the self-expanding stent allowing the self-expanding stent to revert to a non-compressed state.

10. The stent delivery system of claim 9, wherein:
the self-expanding stent further comprises an outer diameter, wherein the outer diameter of the self-expanding stent during the delivery state is smaller than the outer diameter of the self-expanding stent during the deployed state.

11. The stent delivery system of claim 1, wherein:
the first individually movable pull member has a predetermined built in amount of slack.

12. A method of delivering a stent, comprising:
providing a stent delivery system comprising a self-expanding stent comprising a longitudinal length, a plurality of individual suture loops spaced along the longitudinal length of the self-expanding stent, wherein the self-expanding stent is compressed by the plurality of individual suture loops, the individual suture loops comprise a first set of individual suture loops and a second set of individual suture loops, a first longitudinal pull member securing the first set of individual suture loops about a first portion of the self-expanding stent, and a second longitudinal pull member securing the second set of individual suture loops about a second portion of the self-expanding stent, wherein the first set of individual suture loops are configured to separate from about the self-expanding stent when the first longitudinal pull member is removed, the second set of individual suture loops are configured to separate from about the self-expanding stent when the second longitudinal pull member is removed, and a main pull member, the main pull member connected to the first individually movable pull member and the second individually movable pull member;

inserting the stent delivery system in a compressed state into a body lumen;

expanding the first portion of the self-expanding stent to an expanded state by removing the first longitudinal pull member to separate the plurality of first set of individual suture loops from about the self-expanding stent; and expanding the second portion of the self-expanding stent to an expanded state by removing the second longitudinal pull member to separate the second set of individual suture loops from about the self-expanding stent.

13. The method of claim 12, further comprising:
providing a longitudinal retrieval member connected to the plurality of individual suture loops; and
removing the plurality of individual suture loops from the body lumen by extracting the longitudinal retrieval member.

14. A method of delivering a stent, comprising:
providing a stent delivery system comprising a self-expanding stent comprising a longitudinal length, the longitudinal length comprising a plurality of stent portions, each stent portion comprising a plurality of individual suture loops compressing the corresponding stent portion, and a plurality of longitudinal pull members corresponding to the plurality of stent portions, each longitudinal pull member securing the corresponding plurality of suture loops about the self-expanding stent, wherein the plurality of individual suture loops in each stent portion are configured to separate from about the self-expanding stent when the corresponding longitudinal pull member is removed, and a main pull member, the main pull member connected to a first individually movable pull member and a second individually movable pull member;

inserting the stent delivery system in a compressed state into a body lumen; and expanding one of the plurality of stent portions to an expanded state by removing the corresponding longitudinal pull member to separate the corresponding plurality of individual suture loops from about the self-expanding stent.

15. The method of claim 14, further comprising:
repeating the step of expanding one of the plurality of stent portions until all of the plurality of stent portions are expanded.

16. The method of claim 15, further comprising:
providing a longitudinal retrieval member connected to the plurality of individual suture loops; and
removing the plurality of individual suture loops from the body lumen by extracting the longitudinal retrieval member.

* * * * *

UNITED STATES PATENT AND TRADEMARK OFFICE
CERTIFICATE OF CORRECTION

PATENT NO. : 10,004,620 B2
APPLICATION NO. : 14/992449
DATED : June 26, 2018
INVENTOR(S) : Gerard Treacy et al.

It is certified that error appears in the above-identified patent and that said Letters Patent is hereby corrected as shown below:

In the Claims

In Column 6, Claim 1, at the end of Line 59 and the beginning of Line 60, delete "plurality of individual"

In Column 8, Claim 12, Line 18, delete "plurality of"

Signed and Sealed this
Fourth Day of June, 2019

Andrei Iancu
*Director of the United States Patent and Trademark Office*